(12) United States Patent
Iwase et al.

(10) Patent No.: US 10,034,370 B2
(45) Date of Patent: Jul. 24, 2018

(54) STRETCHABLE CIRCUIT BOARD AND METHOD FOR MANUFACTURING STRETCHABLE CIRCUIT BOARD

(71) Applicant: NIPPON MEKTRON, LTD., Tokyo (JP)

(72) Inventors: Masayuki Iwase, Tokyo (JP); Keizo Toyama, Tokyo (JP)

(73) Assignee: NIPPON MEKTRON, LTD., Tokyo (JP)

(*) Notice: Subject to any disclaimer, the term of this patent is extended or adjusted under 35 U.S.C. 154(b) by 0 days.

(21) Appl. No.: 15/690,976

(22) Filed: Aug. 30, 2017

(65) Prior Publication Data
US 2018/0092206 A1 Mar. 29, 2018

(30) Foreign Application Priority Data

Sep. 28, 2016 (JP) .................. 2016-190348

(51) Int. Cl.
| | |
|---|---|
| *H05K 1/02* | (2006.01) |
| *H05K 3/36* | (2006.01) |
| *H05K 3/06* | (2006.01) |
| *A61B 5/00* | (2006.01) |
| *H05K 1/09* | (2006.01) |
| *H05K 1/11* | (2006.01) |

(52) U.S. Cl.
CPC ......... *H05K 1/0283* (2013.01); *A61B 5/6801* (2013.01); *H05K 1/0281* (2013.01); *H05K 3/06* (2013.01); *H05K 3/361* (2013.01); *A61B 2562/164* (2013.01); *A61B 2562/166* (2013.01); *H05K 1/09* (2013.01); *H05K 1/111* (2013.01); *H05K 2201/09036* (2013.01); *H05K 2201/09054* (2013.01); *H05K 2201/10151* (2013.01)

(58) Field of Classification Search
CPC ............................. H05K 3/361; H05K 1/0283
See application file for complete search history.

(56) References Cited

FOREIGN PATENT DOCUMENTS

| | | |
|---|---|---|
| JP | 2014-162124 A | 9/2014 |
| JP | 2014-236103 A | 12/2014 |

*Primary Examiner* — Jeremy C Norris
(74) *Attorney, Agent, or Firm* — Westerman, Hattori, Daniels & Adrian, LLP (57) ABSTRACT

A stretchable circuit board includes: a stretchable portion 50 that includes a stretchable base 53 having stretchability and a stretchable wiring 55 formed on a first main surface 53*a* of the stretchable base 53 and having stretchability; and a non-stretchable portion 30 that includes a base substrate 34 having stretchability lower than that of the stretchable base 53 and a draw-out wiring 35 formed on a main surface 32*b* of the base substrate 34, in which the main surface 53*a* of the stretchable portion 53 and the main surface 32*b* of the base substrate 34 are joined with each other, and the stretchable wiring 55 and the draw-out wiring 35 are electrically connected with each other. In addition, the main surface 32*b* of the base substrate has a rough surface with projections and depressions.

11 Claims, 6 Drawing Sheets

STRETCHABLE CIRCUIT BOARD AND METHOD FOR MANUFACTURING STRETCHABLE CIRCUIT BOARD

TECHNICAL FIELD

The present invention relates to stretchable circuit boards and methods for manufacturing a stretchable circuit board.

RELATED ART

In the wearable device market and the medical device market, biological sensors and biological information monitors have received much attention in recent years. For example, the sports industry has been making an effort to quantify body movements of competitors in a highly precise manner in order to improve competitors' physical ability or skills. In such a case, wearable biological sensors that sense movement of a living body are used in some occasions. In addition, the medical industry has been detecting vital signs (biological information) such as electrocardiograms, heart rates, blood pressures, and body temperatures for the purpose of treatment of diseases or prevention against diseases. In such a case, biological information monitors may be used to detect these vital signs. In general, these biological sensors or biological information monitors are attached to garments or equipment. Then, sensing or monitoring is performed by wearing these garments or equipment.

However, as a human body moves, these garments or equipment are slightly misaligned from a body. If the biological sensor or the biological information monitor, which is provided to the garment or equipment, is misaligned from the targeted portion of a living body, the sensing accuracy or monitoring accuracy significantly deteriorates.

This problem can be prevented by affixing the biological sensor or biological information monitor directly onto the human body. In order to affixing it directly onto the human body, the biological sensor or the biological information monitor needs to have stretchability. Thus, in recent years, study has been made on stretchable electronics having a base or wiring that can stretch in in-plane directions. For the stretchable electronics, use of stretchable circuit boards that can stretch in association with movement of joints and the like of a human body are proposed. In a case where biological sensors or biological information monitors are used in medical application, it is desired that at least a portion of the biological sensor that is in contact with a living body or used in the vicinity of the living body should be disposable from the viewpoint of prevention of infectious diseases.

As for a known stretchable circuit board, Patent Document 1 describes a circuit board that includes a stretchable base and an electroconductive pattern containing electroconductive microparticles and elastomer. In the case of the circuit board described in Patent Document 1, the entire circuit board has stretchability. Furthermore, Patent Document 2 describes a stretchable circuit board. In this stretchable circuit board, an island made of a material having Young's modulus higher than that of a stretchable base is embedded in the base. Embedding of the island described in Patent Document 2 is performed by forming a thin membrane through a printing method. This island has elements mounted thereon, and individual islands are connected with each other by stretchable wires. This document describes that, with this configuration in which islands are connected with each other by stretchable wires, it is possible to prevent elements from breaking or prevent breakage of wires extending over a boundary between the island and the base when the stretchable base stretches.

RELATED DOCUMENT

Patent Document

Patent Document 1: Japanese Patent Application Laid-open No. 2014-216103
Patent Document 2: Japanese Patent Application Laid-open No. 2014-162124

SUMMARY OF THE INVENTION

Problem to be Solved by the Invention

Meanwhile, the stretchable circuit board includes a portion that is to be attached to an uneven surface or curved surface, and a portion that outputs inputted signals to the outside. The portion to be attached to the uneven surface has stretchability, and the portion that outputs the signals to the outside has hardness sufficient to withstand insertion/extraction of a connector. Thus, the stretchable circuit board has a portion having stretchability and a portion not having stretchability or a portion having reduced stretchability (here, portion not haying stretchability), and the stretchable circuit board is configured by bonding these portions to each other. The base of the portion having stretchability is, for example, a sheet-like member made out of elastomer material. In addition, the base of the portion not having stretchability is, for example, a film made out of a material of polyethylene terephthalate (PET). Bonding of the base to the film is performed through laminate connection in which both are compressed and heated.

The stretchable circuit board is attached, for example, to the uneven surface in a state of being aligned with the uneven surface and the like, for the purpose of precisely obtaining signals from the uneven surface. Thus, the stretchable circuit board is subjected to force in in-plane directions at the time of attachment. Furthermore, in some cases, bonding with the stretchable substrate may not be correctly performed. If bonding is not correctly performed, the stretchable substrate is detached from the uneven surface or the like and is bonded again. At this time, force is also applied to the stretchable substrate. For such a stretchable substrate, relatively large stress acts on the boundary between the stretchable portion and the portion not having stretchability, which may lead to both being detached. Thus, the stretchable substrate is required to have an increased joining strength between the stretchable portion of the stretchable substrate and the portion not having stretchability.

However, no description is made in Patent Document 1 and Patent Document 2 as to joining of the base having stretchability with the film not having stretchability.

The present invention has been made in view of the points described above, and provides a stretchable circuit board having an increased joining strength between a portion having stretchability and portion not having stretchability, and a method for manufacturing the stretchable circuit board.

Means for Solving the Problem

A stretchable circuit board according to one aspect of the present invention includes:

a stretchable portion that includes a stretchable base having stretchability and a stretchable wiring formed on a first main surface of the stretchable base and having stretchability; and a non-stretchable portion that includes a base substrate having stretchability lower than that of the stretchable base and a draw-out wiring formed on a first main surface of the base substrate, in which the first main surface of the stretchable base and the first main surface of the base substrate are joined with each other, the stretchable wiring and the draw-out wiring are electrically connected with each other, and the first main surface of the base substrate is a rough surface having a projection and a depression.

A method for manufacturing a stretchable circuit board according to another aspect of the present invention includes:

etching a metal foil of a base substrate and exposing a rough surface having a projection and a depression, the base substrate including the rough surface and the metal foil formed on the rough surface; and bonding a stretchable portion, which includes a stretchable base having stretchability higher than that of the base substrate and also includes a stretchable wiring formed on a first main surface of the stretchable base and having stretchability, to the base substrate such that the stretchable base and the stretchable wiring are joined with the rough surface.

Effect of the Invention

The stretchable circuit board and the method for manufacturing the stretchable circuit board according to the present invention can provide a stretchable circuit board having an increased joining strength between a portion having stretchability and portion not having stretchability, and a method for manufacturing the stretchable circuit board.

DETAILED DESCRIPTION

Hereinbelow, the first, second, and third exemplary embodiments, each of which relates to a stretchable circuit board and a method for manufacturing a stretchable circuit board according to the present invention, will be described.

First Exemplary Embodiment (Stretchable Circuit Board)

Figure 1A:
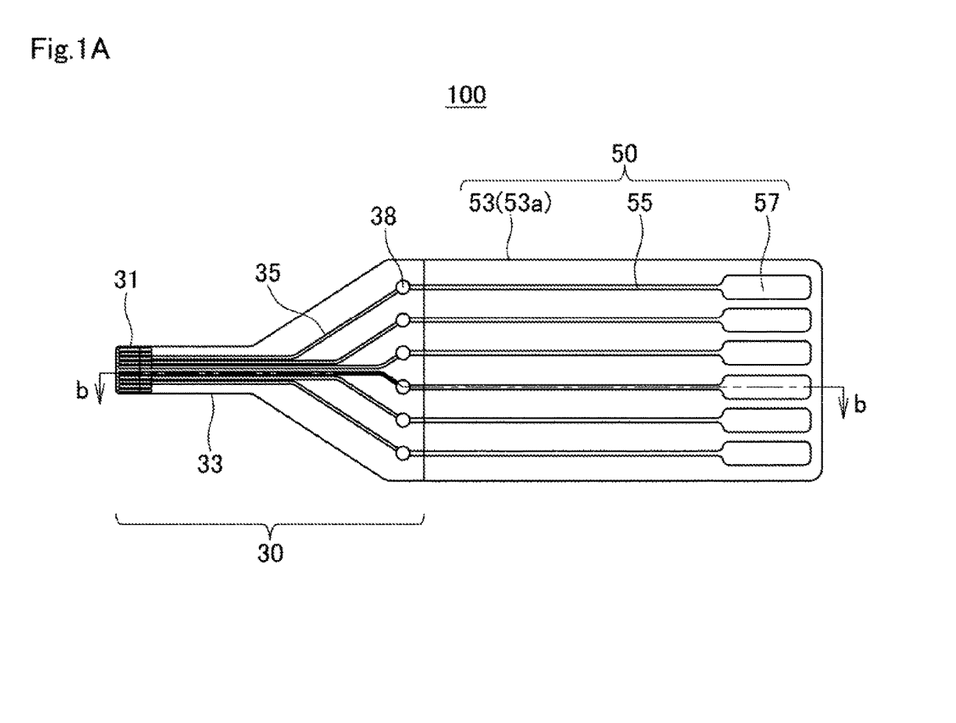
FIGS. 1A and 1B are diagrams for explaining a stretchable circuit board according to a first exemplary embodiment of the present invention.
Figure 1B:
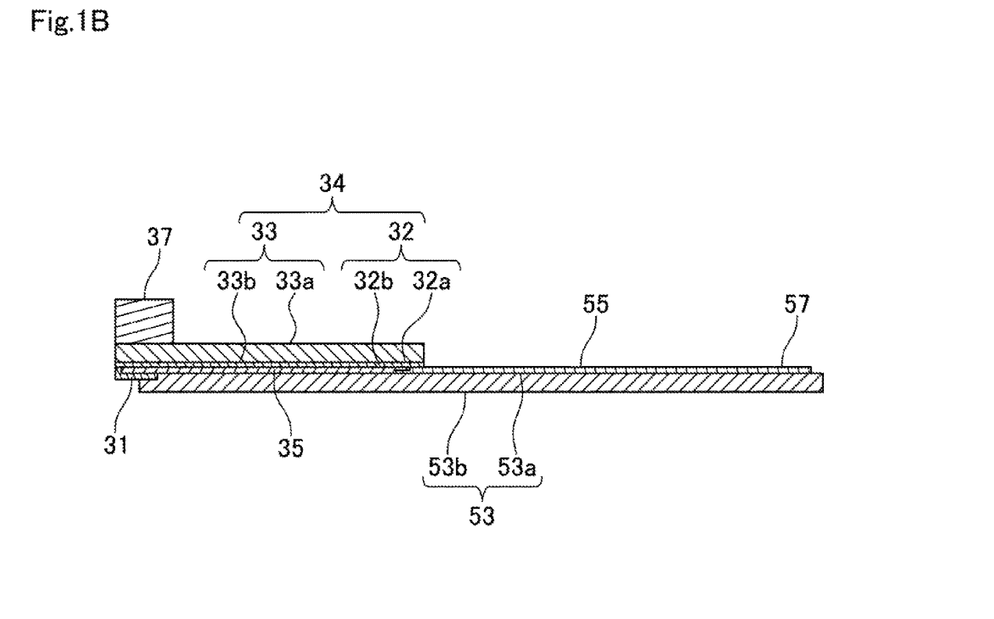
Figure 2:
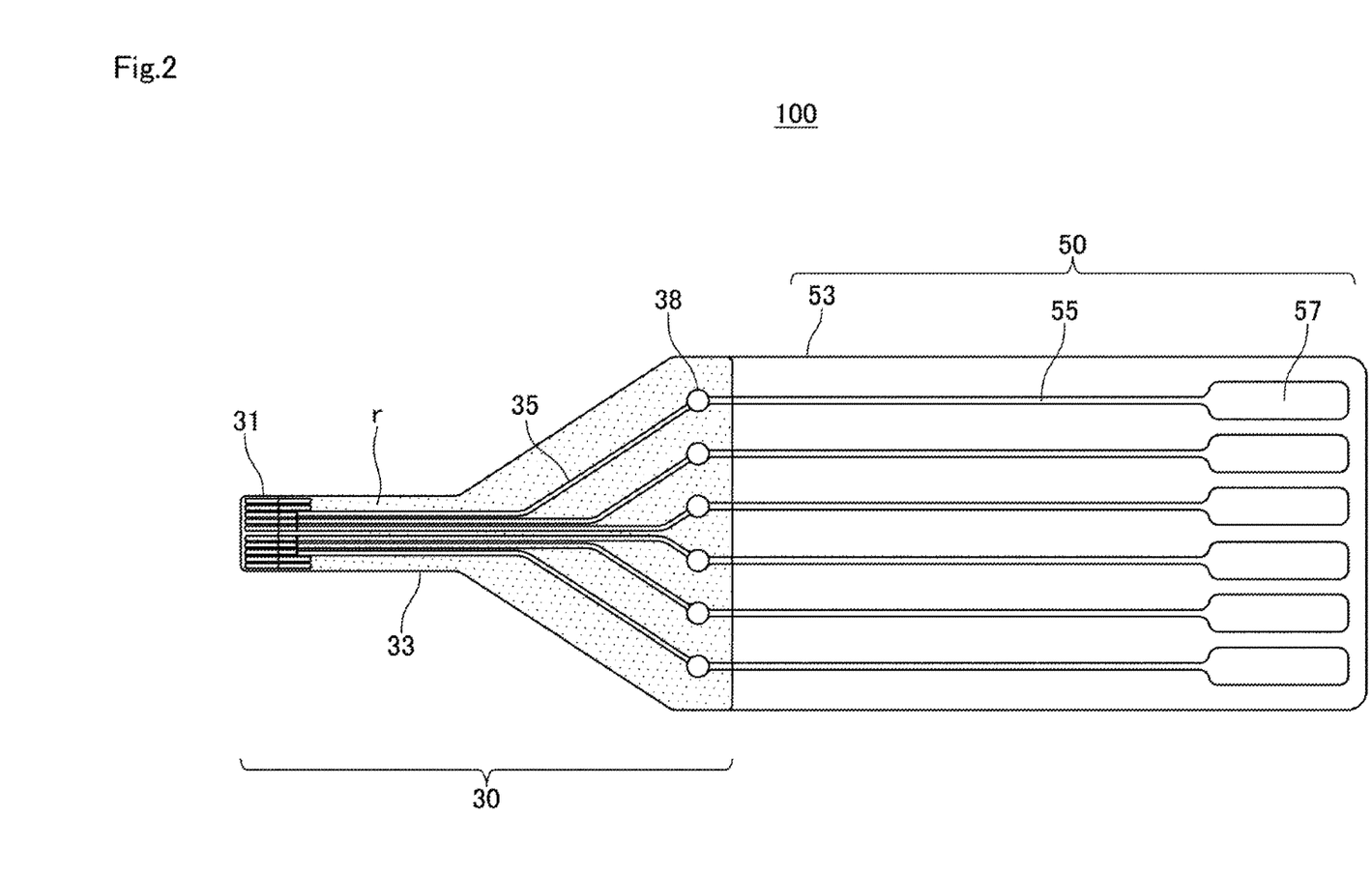
FIG. 2 is a diagram for explaining a layer having a draw-out wiring illustrated in FIGS. 1A and 1B formed thereon.
Figure 3A:
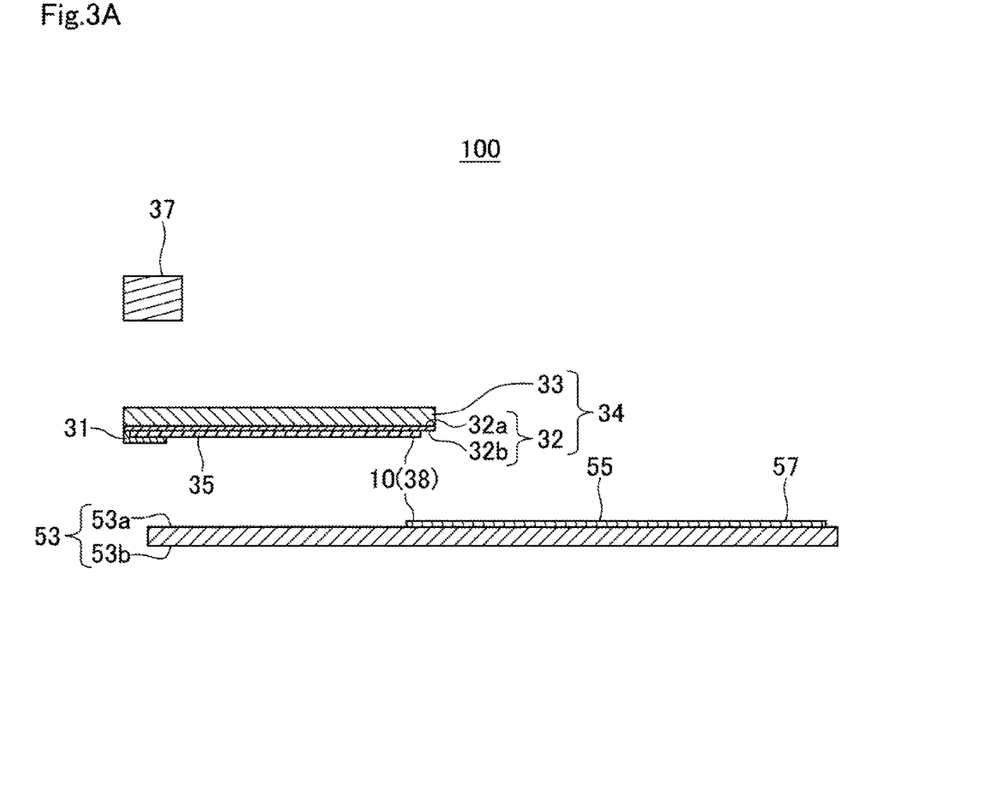
FIGS. 3A and 3B are diagrams for explaining a method for manufacturing the stretchable circuit board according to the first exemplary embodiment.
Figure 3B:
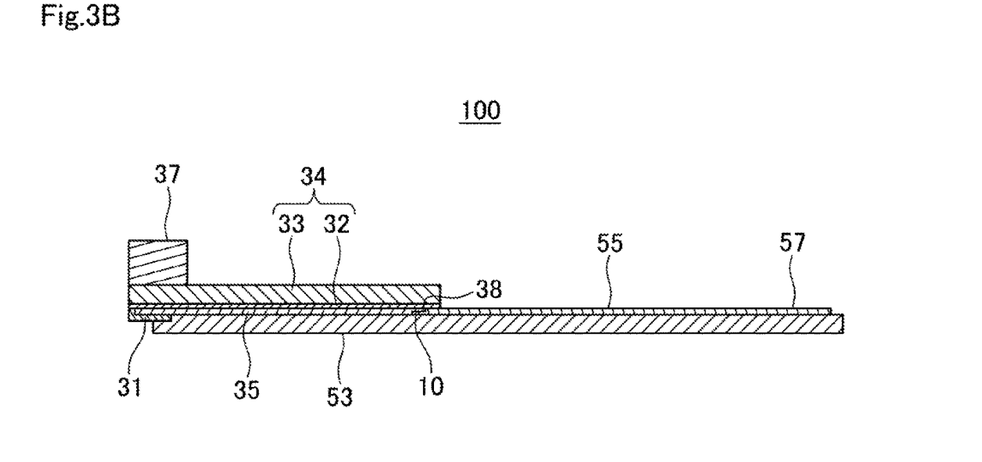

FIGS. 1A and 1B are diagrams for explaining a stretchable circuit board 100 according to the first exemplary embodiment. FIG. 1A is a top view illustrating the stretchable circuit board 100. FIG. 1B is a sectional view taken along the long dashed short dashed line b-b in FIG. 1A. FIG. 2 is a diagram for explaining a layer having a draw-out wiring 35 illustrated in FIGS. 1A and 1B formed thereon. FIGS. 3A and 3B are diagrams for explaining a method for manufacturing the stretchable circuit board 100 according to the first exemplary embodiment. Note that, in each of the drawings, corresponding constituent components are denoted as the same reference characters, and detailed explanation thereof will not be repeated as appropriate.

It should be noted that the "plane" as used in this specification is not required to be geometrically completely flat, and is allowed to have a recessed portion or a protruding portion formed thereon. Furthermore, the "film" as used in this specification broadly includes a thing that generally has a thin thickness shape, such as a sheet and a film-shaped thing. In other words, as for the terms "sheet," "film," "film-shaped thing," and the like, difference in name does not define the thickness size of the thing.

In addition, in the following description of the first exemplary embodiment, the bottom side in the drawings may be called a lower surface side, and the top side may be called an upper surface side, for the purpose of convenience. However, these directions are defined for the purpose of convenience with the aim of illustrating relative positional relationships of constituent elements, and do not necessarily match the top or bottom in the gravity direction.

A stretchable circuit board 100 according to the first exemplary embodiment includes a stretchable portion 50, which includes a stretchable base 53 having stretchability and a stretchable wiring 55 formed on a first main surface 53a of the stretchable base 53 and having stretchability. Furthermore, the stretchable portion 50 according to the first exemplary embodiment includes a stretchable electrode 57 formed on an end portion of the stretchable wiring 55. In addition, the stretchable circuit board 100 also includes a non-stretchable portion 30, which includes a base substrate 34 having stretchability lower than that of the stretchable base 53 and a draw-out wiring 35 formed on a first main surface of the base substrate 34 and having stretchability lower than that of the stretchable wiring 55. In the first exemplary embodiment, the base substrate 34 has a film-like film base 33 and an anchor layer 32 disposed between the film base 33 and the draw-out wiring 35. The main surface having the draw-out wiring 35 disposed thereon is a main surface 32b of the anchor layer 32 of the base substrate 34.

Furthermore, in the stretchable circuit board 100, the main surface 53a of the stretchable base 53 and the main surface 32b of the anchor layer 32 of the base substrate 34 (hereinafter, also simply referred to as "main surface 32b of the anchor layer 32") are joined with each other, and the stretchable wiring 55 and the draw-out wiring 35 are electrically connected. As illustrated in FIG. 1B and FIG. 2, the main surface 32b of the anchor layer 32 is a rough surface r (portion shown as a shaded portion) having projections and depressions (texture). Note that, in FIG. 2, the area of the rough surface r is schematically illustrated so as to be layered with the film base 33.

In the configuration described above, the "main surface" represents a surface having an area significantly greater than those of other surfaces of all the surfaces of the thin sheet. As the circuit board is a thin sheet, a surface having an area similar to that of the main surface exists on the back side of the main surface, and in the first exemplary embodiment, this back surface is also regarded as the "main surface."

Furthermore, in the configuration described above, the "main surface 53a of the stretchable base 53 and the main surface 32b of the anchor layer 32 are joined with each other" means that heat and pressure are applied to the main surface 53a and the main surface 32b, and they are directly brought into contact with each other'to be integrated into one (laminate connection). However, in the present specification, an adhesive or pressure-sensitive adhesive agent may be used as appropriate to join other layers with each other (for example, a stretchable supporting member or stretchable cover, which will be described later).

In addition, in the configuration described above, the rough surface represents a surface having projections and depressions of which surface roughness is, for example, more than or equal to Rz of 0.5 μm in terms of evaluation by 10-point average roughness. Note that, although the 10-point average will be described later, such a standard is defined in a specification of "JIS B 0601: 2001" of the Japanese Industrial Standards.

Below, the configuration described above will be sequentially described.

(Stretchable Base)

The stretchable base 53 has stretchability higher than that of the film base 33. A preferable base material forming the stretchable base 53 includes an elastomer material such as nitrile rubber, latex lubber, urethane-based elastomer, and silicone-based elastomer. However, the base material is not limited to these materials. In particular, by employing a urethane-based elastomer sheet used in medical application, it is possible to enhance safety even in the case where it is attached on the skin of a human body.

It is preferable that the stretchable base 53 has the maximum elongation percentage of not less than 10%, more preferably, of not less than 50%, still more preferably, of not less than 100%, and still more preferably, of not less than 200%. If the stretchable base 53 is made from the base material described above, it is possible to achieve the maximum elongation percentage, for example, of not less than 300%. Here, the maximum elongation percentage of the stretchable base 53 represents the maximum value of percentage of elongation in terms of elastic deformation in one direction in in-plane directions.

It should be noted that the elongation percentage as used in this specification represents a ratio of elongation in one direction in in-plane directions caused by application of force relative to the size in the case where no external force is applied (size at the time of elongation percentage of 0%). For example, in the case of the elongation percentage of 50%, the size of the substance is 1.5 times the size at the time of the elongation percentage of 0%. In the case of the elongation percentage of 100%, the size of the substance is twice the size at the time of elongation percentage of 0%.

No particular limitation is applied to the thickness of the stretchable base 53. However, it is preferable to set the thickness of the base, for example, to not more than 100 μm from the viewpoint of not blocking stretching movements of the target (target surface) to which the stretchable circuit board 100 is applied. More desirably, the thickness of the stretchable base 53 is not more than 25 μm, and still more desirably, is not more than 10 μm.

(Stretchable Wiring)

As illustrated in FIG. 1A and FIG. 2, the stretchable wiring 55 has one end portion connected with a connection end portion 38 of the draw-out wiring 35. This connection is performed, for example, through laminate connection or application of pressure. The stretchable wiring 55 has the other end portion connected with the stretchable electrode 57.

The thickness size and the width size of the stretchable wiring 55 may be determined on the basis of resistivity of the stretchable wiring 55 at no load, a change in resistance of the stretchable base 53 when it is stretched, and restriction on the thickness size and the width size of the entire stretchable circuit board 100. The width size of the stretchable wiring 55 is set preferably to not more than 1000 μm, more preferably to not more than 500 μm, still more preferably to not more than 200 μm, from the viewpoint that the stretchable wiring 55 can follow a change in sizes of the stretchable base 53 at the time of stretching to achieve favorable stretchability. The thickness size of each wire constituting the stretchable wiring 55 may be set to not more than 25 μm, and be set desirably to be not less than 10 μm and not more than 15 μm.

The stretchable wiring 55 is configured by containing an electrically conductive material, and thus, has electrical conductivity. For the electrically conductive material forming the stretchable wiring 55, it may be possible to select a material having preferable electrical conductivity such as silver, gold, platinum, carbon, copper, aluminum, cobalt, and nickel, or an alloy thereof. The shape of the electrically conductive material is not particularly limited. However, it may be possible to use a particle-like shape such as a granule and powder. There is no particular limitation to the shape of the particle. However, it may be possible to use a spherical shape, a needle shape, a flake shape, a nanowire shape, or the like.

It is preferable that the stretchable wiring 55 further contains a resin binder. The stretchable wiring 55 according to the first exemplary embodiment is made from an electrically conductive material prepared in a manner such that electrically conductive particles are dispersed in a resin material. Since the stretchable wiring 55 contains a resin binder, it is possible to prevent the stretchable wiring 55 from breaking due to stretching of the stretchable base 53. The resin binder includes, for example, a thermoplastic elastomer material such as a urethane resin binder and an acrylic resin binder. However, the resin binder is not limited to this. It is desirable to select a resin binder having reduced Young's modulus so that the elastic modulus of the stretchable wiring 55 in a filmed state is less than or equal to that of the stretchable base 53. One single type of elastomer material may be used for the resin binder, or plural types of elastomer materials may be mixed and be used.

(Base Substrate)

The base substrate 34 includes the film base 33 and the anchor layer 32. The draw-out wiring 35, which will be described later, is formed on the main surface 32b of the anchor layer 32. Note that the base substrate 34 has stretchability lower than that of the stretchable base 53, and unlike the stretchable base 53, the base substrate 34 does not have the maximum elongation percentage of not less than 10%.

(Film Base)

The film base 33 is a member having flexibility, and has Young's modulus higher than that of the stretchable base 53. Note that, in the first exemplary embodiment, the film base 33 has stretchability lower than that of the stretchable base 53, and is a member that substantially does not stretch. There is no particular limitation to the material of the film base 33. However, it may be possible to use a synthetic resin having a low sliding resistance property, corrosion resistance, and increased strength, such as polyethylene terephthalate (PET), polyethylene naphthalate (PEN), polyimide (PI), polyphene sulfide (PPS), and fluorocarbon resin. In addition, for the film base 33, it may be possible to use a paper-based material having appropriate durability such as a cellulose nanofibers paper.

The thickness of the film base 33 may be set to be not less than 10 μm and not more than 200 μm, desirably to be not less than 25 μm and not more than 150 μm, and more desirably to be not less than 50 μm and not more than 100 μm. Furthermore, it is preferable that the thickness of the film base 33 is larger than that of the stretchable base 53. By setting the thickness of the film base 33 so as to fall in the range described above, it is possible to sufficiently increase in-plane rigidity of the non-stretchable portion 30, and reduce the entire thickness of the stretchable circuit board 100.

In the present specification, the main surface of the film base 33 is referred to as a main surface 33a, 33b, and the main surface 33a and the main surface 33b are in relationship of the front and rear sides of the same base.

(Anchor Layer)

The anchor layer 32 has the main surface 32b that is the rough surface r having projections and depressions. The anchor layer 32 is a resin layer having a thickness, for example, of not less than 5 μm and not more than 15 μm. Note that the thickness of the resin layer is not the coating thickness of the resin but is the thickness after cure. The thickness of the resin layer is measured, for example, using a measuring instrument that measures the film thickness in a mechanical manner (micrometer), an optical manner (reflection mirror), or an electrical manner (electromagnetic induction). In addition, this measurement is performed in accordance with the standard of "JIS K 7130: 1999." The thickness of the anchor layer 32 having a surface with projections and depressions may be obtained, for example, by measuring the thickness of the anchor layer 32 at plural points on the anchor layer 32 and calculating an average thereof.

For the resin, acrylic-based resin or epoxy-based resin is used. In the first exemplary embodiment, the anchor layer 32 is formed as a thermosetting-type or ultraviolet-curing-type adhesive layer used for adhesion of a copper foil to the film base 33 to obtain, for example, a copper clad laminate (CCL).

In the first exemplary embodiment, the anchor layer 32 can be formed, for example, through the following method.

In the first exemplary embodiment, the film base 33 is first coated with an adhesive, and a metal foil is attached thereon to obtain a so-called three-layered metal-attached substrate (hereinafter, referred to as a "three-layer substrate"). At the time of manufacturing the three-layer substrate, the surface of the metal foil is subjected to, for example, chemical processing using manganese peroxide or the like to form projections and depressions on the surface of the metal foil in order to enhance adhesiveness of the adhesive. After attaching is performed to the film base 33, the adhesive is cured and hardened in the completed CCL, and loses adhesiveness resulting in a resin layer.

The inventor of the present invention performed patterning of the metal foil so as to match the shape of the draw-out wiring 35 to form the non-stretchable portion 30 having the draw-out wiring 35. After etching is performed at the time of patterning for the draw-out wiring 35, the cured adhesive layer becomes the anchor layer 32 exposed at a portion of the film base 33 where the draw-out wiring 35 does not exists. The projections and depressions located on the surface of the metal foil are transferred to the main surface 32b of the anchor layer 32, and hence, the main surface 32b of the anchor layer 32 is formed into the rough surface r having projections and depressions.

The degree of projections and depressions of the rough surface r can be quantified, for example, using surface roughness. In the first exemplary embodiment, the surface roughness of the rough surface r is quantified using 10-point average roughness (Rz). In the case of the 10-point average roughness (Rz), roughness curves are obtained by measuring projections and depressions on the rough surface r using a measuring instrument such as a measuring microscope, 3-D measuring device, an image-based measuring device, and an electric micrometer. Peaks of the projections and the depressions are extracted from the roughness curve in an area having a predetermined length. The average of the values of the top five peak values in the projection direction is calculated, and the average of the values of the top five peak values in the depression direction is calculated, The difference between these average values in a unit of micrometer represents a value of the 10-point average roughness (Rz). In the first exemplary embodiment, the 10-point average roughness Rz of the main surface 32b of the anchor layer 32 is set to be not less than 0.5 μm and not more than 5 μm.

Furthermore, in the first exemplary embodiment, the thickness of the anchor layer 32 and the roughness of the surface of the anchor layer 32 are not limited to those expressed by an absolute value. For example, in the first exemplary embodiment, the 10-point average roughness Rz may be expressed as a ratio based on the thickness of the anchor layer 32. In such a case, the 10-point average roughness Rz may be set, for example, to be not less than 5% of the anchor layer 32 and not more than 40%.

Furthermore, the anchor layer 32 is not limited to the one formed using an adhesive as described above. For example, it is possible to obtain the anchor layer 32 having a similar configuration by coating the surface of the film base 33 having rough surface with a metal thin membrane, and etching the metal thin membrane through a photolithography method. Alternatively, it is possible to obtain the anchor layer 32 having a similar configuration by forming a thin membrane having a surface with an insulating property on the film base 33, forming a metal thin membrane on the rough surface, and applying etching.

(Draw-Out Wiring)

Furthermore, the draw-out wiring 35 may have stretchability, or may not have stretchability. In the first exemplary embodiment, the draw-out wiring 35 is formed through etching. In the first exemplary embodiment, the draw-out wiring 35 can be created by affixing a metal foil, which has been formed into a sheet shape, on the main surface 33b of the film base 33 with an adhesive, and etching the metal foil into a desirable pattern shape of the draw-out wiring 35. The metal foil may be made out of for example, copper, nickel, silver, aluminum, and so on.

In the case where the draw-out wiring 35 is created by etching the metal foil, the draw-out wiring 35 substantially does not have a fusing property. Thus, the fusing property of the stretchable base 53 containing an elastomer material as a resin binder enables the end portion of the draw-out wiring 35 and the end portion of the stretchable wiring 55 to be joined together at the connection end portion 38.

Furthermore, in the first exemplary embodiment, in order to minimize the resistance value of the draw-out wiring 35 extending from the external terminal 31 to the connection end portion 38, the material of the draw-out wiring from among these members contains copper. The connection end portion 38, which connects the draw-out wiring 35 and the stretchable wiring 55, may be a base made of a material containing copper, or may be a member subjected to plating processing. Plating may be performed with at least one of tin (Pb) and solder.

(External Terminal)

Furthermore, in the first exemplary embodiment, the main surface 33b of the film base 33 includes terminals each electrically connected with the draw-out wiring 35. In the first exemplary embodiment, this terminal is an external terminal 31 for outputting electrical signals detected by the stretchable electrode 57, to an external device. In the first exemplary embodiment, gold plating is applied to the external terminal 31.

Note that plating of the external terminal 31 in the first exemplary embodiment is not limited to one made of a gold material. For example, it may be possible to employ tin (Pb), nickel (Ni), Zinc (Zn) and a soldering material.

(Reinforcing Member)

In the first exemplary embodiment, a reinforcing member 37 is provided on the back side of a position where the external terminal 31 is formed. Here, the position of "back side of a position where the external terminal 31 is formed" means a location corresponding to the position on the main surface 33b serving as the back surface of the main surface 33a and having the external terminal 31 formed thereon and at which the external terminal 31 is formed. The reinforcing member 37 is a spacer member for adjusting the thickness of the distal end portion of the non-stretchable portion 30 so as to have the accuracy set, for example, for a connector (not illustrated) of an external device when the terminal portion 31 is fitted, for example, to this connector and is connected with this external device.

As for a material for forming the reinforcing member 37, it may be possible to use a synthetic resin having a low sliding-resistance property, corrosion resistance, and increased strength, such as PET, PEN, and PI, or it may be possible to use a paper base material. The reinforcing member 37 may be made from the same type of material as the film base 33, or may be made from a material that belongs to a different type from a material type for the film base 33. In addition, a thin sheet-like metal plate may be used for the reinforcing member 37. When the reinforcing member 37 is joined with the film base 33, it may be possible to use a general pressure-sensitive adhesive or adhesive.

[Method for Manufacturing Stretchable Circuit Board]

Next, a method for manufacturing a stretchable circuit board according to the first exemplary embodiment will be described.

FIGS. 3A and 3B are diagrams for explaining a method for manufacturing the stretchable circuit board according to the first exemplary embodiment. FIGS. 3A and 3B are sectional views taken along the long dashed short dashed line b-b in FIG. 1A. FIG. 3A illustrates that a part of the configuration of the stretchable circuit board 100 is separated for the purpose of explaining each step, and FIG. 3B illustrates a state where the steps for manufacturing each component illustrated in FIG. 3A have been completed.

As illustrated in FIGS. 3A and 3B, the method for manufacturing a stretchable circuit board according to the first exemplary embodiment includes a step of etching a metal foil of the base substrate 34, which includes the main surface 32a having a rough surface with projections and depressions and also includes the metal foil formed on the rough surface (main surface 32a), to form the draw-out wiring 35, and exposing the rough surface. In this step, as illustrated in FIG. 3A, the film base 33 is coated with an adhesive containing an acrylic-based resin or epoxy-based resin, and on the adhesive, a metal foil having a surface subjected to chemical processing to have texture is adhered so that the surface having the chemical processing applied thereon faces the adhesive. Then, the adhesive is cured by heat or ultraviolet light. After this, the entire surface, located on the opposite side to the adhesive layer, of the metal foil is coated with a known resist material. The resist material is selectively hardened by lithography to form the draw-out wiring 35.

Next, wet etching is performed as in-line to the configuration described above, and portions of the metal foil other than the draw-out wiring 35 are removed. At this time, the layer of the adhesive, which serves as the base of the metal foil, remains on the entire surface of the film base 33 as the anchor layer 32. The texture on the surface of the metal foil has been transferred to the main surface 32b of the anchor layer 32, and hence, the entire surface of the film base 33 except for the draw-out wiring 35 is formed into the rough surface r having projections and depressions.

It should be noted that, in the first exemplary embodiment, a monomolecular film based on an organic component is formed on the surface of the draw-out wiring 35 immediately after the etching, for the purpose of preventing corrosion. Such a monomolecular film does not contribute to electric resistance of the draw-out wiring 35. In addition, the monomolecular film does not contribute to a joining performance. Thus, in the first exemplary embodiment, even if the draw-out wiring 35 and the stretchable wiring 55 are joined with each other in a state where the monomolecular film is attached on the surface of the draw-out wiring 35, this state is regarded as the draw-out wiring 35 and the stretchable wiring 55 being joined directly with each other.

Next, the external terminal 31 is formed on the main surface 32b. The external terminal 31 can be created by layering a plating member such as nickel and gold on the draw-out wiring 35 immediately after the etching. With these plating films, it can be expected to prevent ion migration that may happen at the external terminal portion where pitches thereof are relatively narrow, or improvement in wear resistance can be expected.

Next, in the method for manufacturing the stretchable circuit board according to the first exemplary embodiment, the stretchable portion 50 (FIGS. 1A and 1B) and the base substrate 34 are bonded with each other as illustrated in FIG. 3B. In this step, the stretchable portion 50, which includes the stretchable base 53 and the stretchable wiring 55, is bonded to the base substrate 34 so as to be joined with the main surface 32b (rough surface).

In the step described above, the draw-out wiring 35 formed on the base substrate 34 is joined at the connection end portion 38. The surface of the draw-out wiring 35 at the joining portion 10 with the stretchable wiring 55 may be formed only by a material (base) containing copper, or plating with tin or solder may be applied to this surface as described above.

In other words, in the method for manufacturing the stretchable circuit board according to the first exemplary embodiment, the stretchable wiring 55 is formed on the main surface 53a of the stretchable base 53. There is no particular limitation to the method of forming the stretchable wiring 55. However, this stretchable wiring can be formed, for example, through a printing method. With the printing method, the stretchable wiring 55 according to the first exemplary embodiment is a printed pattern formed by printing and applying an electroconductive paste having stretchability. This printed pattern is formed through, after coating of the electroconductive paste, heating the electroconductive paste for a predetermined period of time, and drying it to be hardened.

Although there is no particular limitation as to the printing method, examples of the printing method include a screen printing method, an inkjet printing method, a gravure printing method, and an offset printing method. Of these methods, screen printing is preferably used from the viewpoint of fine resolution or stability in thick membrane.

In the case where the stretchable wiring 55 is formed through the printing method, it is preferable to prepare an electroconductive paste containing the electrically conductive particle described above, the resin binder, and an organic solvent, and use the prepared one in the printing method. By using a stretchable electroconductive paste containing, as the primary component, metal particle such as silver to form the stretchable wiring 55, it is possible to achieve the elongation percentage, for example, of approximately not less than 50% and not more than 70%, and also form a wiring exhibiting an excellent stretching property.

Next, the film base 33 and the stretchable base 53 are overlaid so that the end portion of the stretchable wiring 55 has electric conductivity with the end portion of the draw-out wiring 35 at the connection end portion 38, and then, heat and pressure are applied to them. At this time, conditions are 100° C. for heating and 2 MPa for pressure.

Through the processes described above, the non-stretchable portion 30 (FIGS. 1A and 1B) and the stretchable portion 50 (FIGS. 1A and 1B) are joined with each other through laminate connection. At this time, the stretchable base 53 is melted and enters projections and depressions of the rough surface in the vicinity of the draw-out wiring 35, and provides a strong adhesive force with the anchor layer 32.

The present inventor checked the strength of the joining between the non-stretchable portion 30 and the stretchable portion 50 in the following manner after completion of the stretchable circuit board 100 that has been manufactured through the steps described above. It is known that the stretchable wiring 55 of the stretchable portion 50 increases its resistance when the stretchable base 53 stretches by 70%, and loses a function as the wiring. The present inventor pulled the stretchable portion 50 so as to reach an elongation percentage of 70% while fixing the non-stretchable portion 30. As a result, it is confirmed that, although the stretchable wiring 55 did not work as wiring, the non-stretchable portion 30 and the stretchable portion 50 were not stripped from each other or did not break. Accordingly, it can be said that the stretchable circuit board 100 according to the first exemplary embodiment has sufficiently high joining strength between the non-stretchable portion 30 and the stretchable portion 50.

It should be noted that the present invention should not be limited to the exemplary embodiment described above, and various changes, improvements or other modes should be included, provided that the object of the present invention is achieved. For example, the texture of the metal foil is not limited to one formed through chemical processing. It may be possible to form the metal foil by rolling a metal into a shaped sheet to form the texture.

Furthermore, in the first exemplary embodiment, the base substrate 34 is configured by the film base 33 and the anchor layer 32. However, the base substrate 34 may be a single layer of the film base 33. In the case of the single layer of the film base 33, a metal foil and the film base 33 are integrally configured by casting a material of the film base 33 such as polyimide on the metal foil. At this time, the texture of the metal foil is transferred to the surface of the film base 33 with which the metal foil is brought in contact, and this surface serves as the rough surface r. With such a configuration, the rough surface r having projections and depressions is exposed in the vicinity of the draw-out wiring 35 by etching the metal foil to form the draw-out wiring 35. By layering the stretchable base 53 on the film base 33 described above and applying heat and pressure to them, the stretchable base 53 enters the projections and depressions at end portions of the non-stretchable portion 30 and the stretchable portion 50, whereby it is possible to obtain an increased joining strength.

Furthermore, for example, the stretchable circuit board 100 may be provided with an affixing layer (not illustrated) for attaching the stretchable circuit board 100 on the surface of a human body. Depending on applications of the stretchable circuit board 100, the affixing layer may be provided on the upper surface side of the stretchable circuit board 100, or may be provided on the lower surface side. The affixing layer may be made from a gel agent or pressure-sensitive adhesive.

In addition, in the first exemplary embodiment, the surface of the draw-out wiring 35 may be coated with a photosensitive cover to protect the draw-out wiring 35.

Moreover, each constituent element of the stretchable circuit board 100 according to the present invention needs not exist separately. It may be possible to employ, for example, a configuration in which plural constituent elements are formed as one member, a configuration in which one constituent element is formed by plural members, a configuration in which one constituent element forms a part of another constituent element, and a configuration in which a part of one constituent element overlaps with a part of another constituent element.

Second Exemplary Embodiment

Next, a stretchable circuit board according to a second exemplary embodiment of the present invention will be described.

Figure 4A:
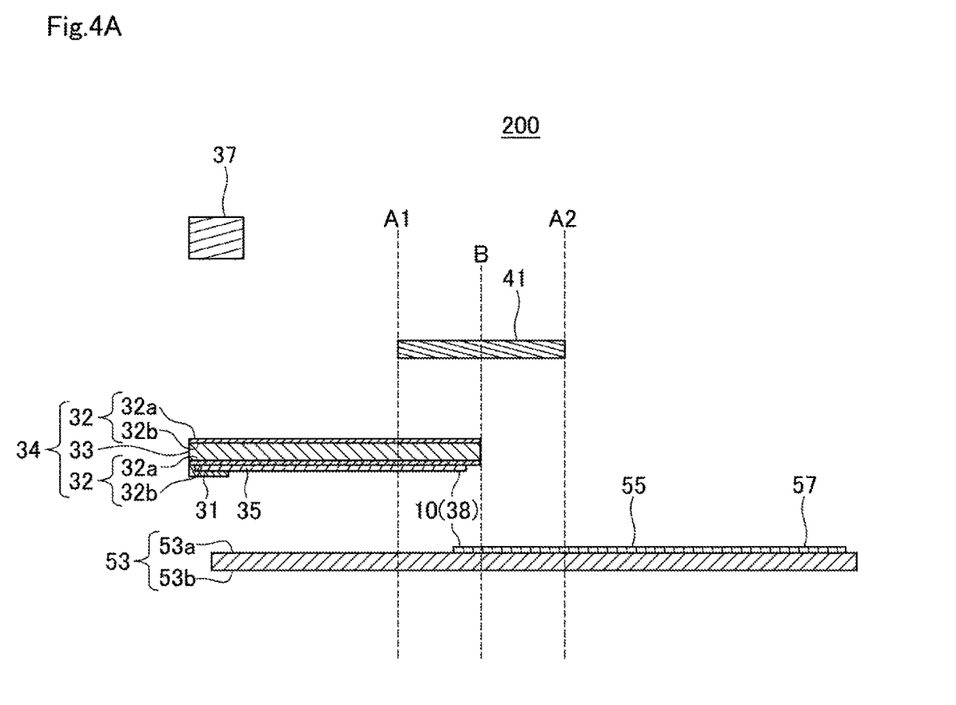
FIGS. 4A and 4B are diagrams for explaining a stretchable circuit board according to a second exemplary embodiment of the present invention.
Figure 4B:
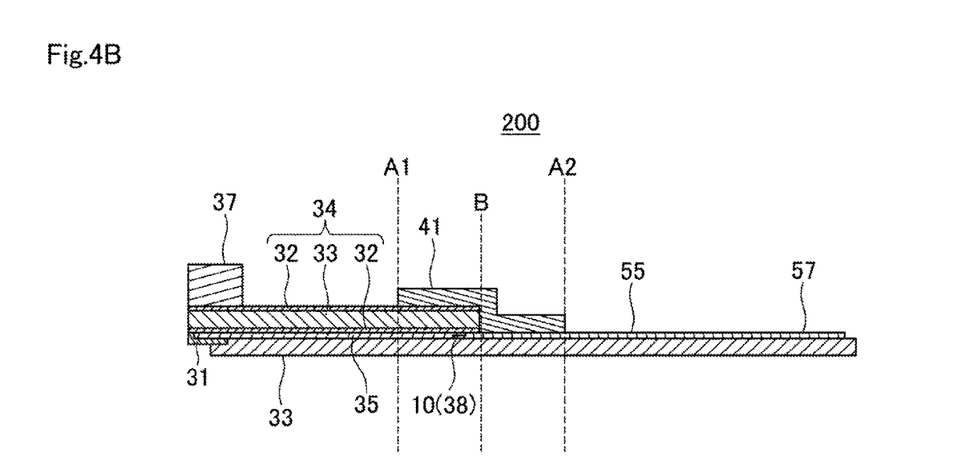

FIG. 4A is a diagram illustrating each configuration of a stretchable circuit board 200 according to the second exemplary embodiment. FIG. 4B illustrates a state where the configurations illustrated in FIG. 4A have been joined with each other. FIGS. 4A and 4B are sectional views taken along the long dashed short dashed line b-b in FIG. 1A.

As illustrated in FIGS. 4A and 4B, in an area A1, A2 including a boundary B between the non-stretchable portion 30 and the stretchable portion 50, the stretchable circuit board 200 according to the second exemplary embodiment has a stretchable supporting member 41 having stretchability equivalent to that of the stretchable base 53 and higher than that of the base substrate 34. Note that the "stretchability equivalent to" as used herein includes stretchability equal to that of the stretchable base 53 and also includes a range of not less than half of the stretchability of the stretchable base 53 and not more than twice thereof.

As illustrated in FIGS. 4A and 4B, the stretchable circuit board 200 according to the second exemplary embodiment has the stretchable supporting member 41. The stretchable supporting member 41 is provided in the area A1, A2 including the boundary B between the non-stretchable portion 30 and the stretchable portion 50, which results in the stretchable supporting member 41 being provided so as to straddle the non-stretchable portion 30 and the stretchable portion 50. More specifically, the stretchable supporting member 41 is provided throughout the entire width of the stretchable circuit board 200 and in an area containing the connection end portion 38 between the draw-out wiring 35 and the stretchable wiling 55.

The stretchable supporting member 41 has stretchability in in-plane directions, and may be made from the same type of elastomer material as the stretchable base 53. In the second exemplary embodiment, a material having stretchability higher than that of the non-stretchable portion 30 and equivalent to that of the stretchable portion 50 is selected for the material of the stretchable supporting member 41. This makes it possible that the stretchable circuit board 200 according to the second exemplary embodiment can distribute stress that may increase at the boundary between the non-stretchable portion 30 and the stretchable portion 50 when the stretchable portion 50 stretches, whereby it is possible to reduce the risk of breakage of the stretchable wiring 55.

Furthermore, in the second exemplary embodiment, the back surface corresponding to the main surface of the base substrate 34 also has a rough surface with projections and depressions, in addition to the first main surface of the base substrate 34, as illustrated in FIGS. 4A and 4B. More specifically, the base substrate 34 according to the second exemplary embodiment includes the film base 33 and anchor layers 32 formed on both surfaces of the film base 33. The main surface 32a, located in the upper portion of the drawings, of the anchor layer 32 of the film base 33 and the main surface 32b, located in the lower portion of the drawings, of the anchor layer 32 of the film base 33 are the rough surfaces r.

This configuration can be obtained, for example, by coating both surfaces of the film base 33 with an adhesive, and attaching metal foils on the film base 33 with the adhesive. Then, the adhesive is cured by heat or ultraviolet light, etching is applied to the entire surface of the main surface 32a, and etching is applied to the main surface 32b through a resist pattern of the draw-out wiring 35.

In the second exemplary embodiment, the stretchable supporting member 41 is provided on the main surface 32a of the anchor layer 32. This configuration not only increases the joining strength between the film base 33 and the stretchable base 53 but also enhances the joining strength between the film base 33 and the stretchable supporting member 41.

Etching to both surfaces of the film base 33 can be performed at the same time by passing the film base 33 through a lane where etching solution is supplied from both sides of the front surface and the back surface of the film base 33. Thus, in the second exemplary embodiment, no additional step is required as both surfaces of the film base 33 are etched. Furthermore, if a copper foil is used as the metal foil in the steps described above, copper can be collected from the etching solution that has been used in etching, and hence, it is possible to reuse copper that has been removed during etching.

In the second exemplary embodiment in which metal foils on both surfaces of the film base 33 are etched at the same time under the same conditions, the average roughness of the first main surface 32a of the base substrate 34 is substantially equal to the average roughness of the main surface 32b that is the back surface of the base substrate 34. Note that the "average roughness is substantially equal" means, for example, that the difference in the 10-point average roughness Rz described above between the main surface 32a and the main surface 32b falls within ±50%.

Third Exemplary Embodiment

Next, a stretchable circuit board according to a third exemplary embodiment of the present invention will be described.

Figure 5A:
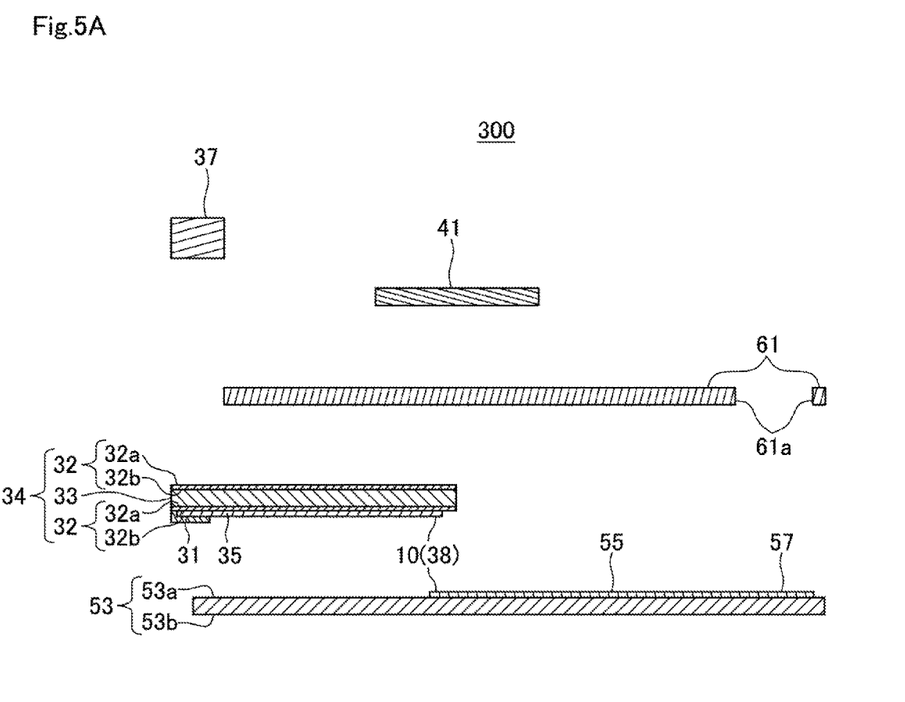
FIGS. 5A and 5B are diagrams for explaining a stretchable circuit board according to a third exemplary embodiment of the present invention.
Figure 5B:
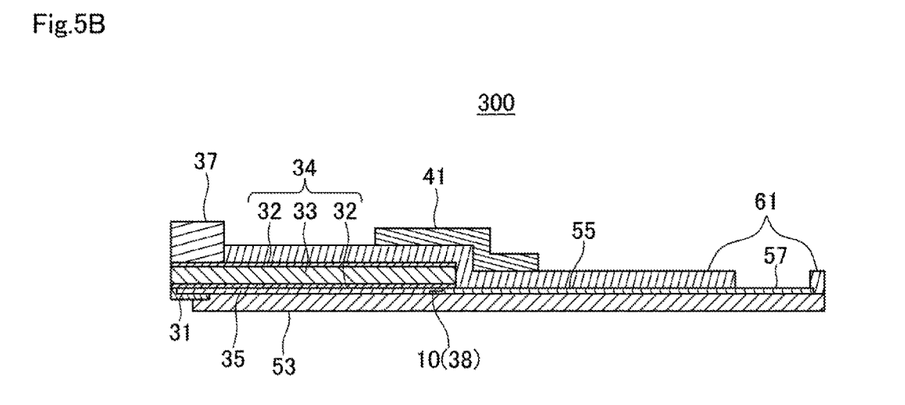

FIG. 5A is a diagram illustrating each configuration of a stretchable circuit board 300 according to the third exemplary embodiment. FIG. 5B illustrates a state where the configurations illustrated in FIG. 5A have been joined with each other. FIGS. 5A and 5B are sectional views each taken along the long dashed short dashed line b-b in FIG. 1A.

In the stretchable circuit board 300, a stretchable cover 61 covering at least part of the stretchable wiring 55 and having stretchability is joined directly with the main surface 32a of the base substrate 34.

In the case of the stretchable circuit board 300 according to the third exemplary embodiment, the base substrate 34 has the film base 33 including anchor layers 32 formed on both surfaces as in the second exemplary embodiment. The main surface 32a, located in the upper portion of the drawings, of the anchor layer 32 of the film base 33 is the rough surface r as with the main surface 32b, located in the lower portion of the drawings, of the anchor layer 32 of the film base 33. Thus, in the third exemplary embodiment, it is possible to obtain increased joining strength between the main surface 32a and the stretchable cover 61.

(Stretchable Cover)

The stretchable cover 61 is a stretchable sheet-like cover that covers the main surface 32a of the base substrate 34 and the main surface 53a of the stretchable base 53. The stretchable cover 61 according to this exemplary embodiment is formed into a size that not only extends over the stretchable portion 50 but also reaches the non-stretchable portion 30. The stretchable cover 61 illustrated in FIGS. 5A and 5B, together with the stretchable supporting member 41, covers the non-stretchable portion 30 and the stretchable portion 50 from the upper surfaces of the non-stretchable portion 30 and the stretchable portion 50 in the drawings. In addition, the stretchable cover 61 has an opening 61a for the stretchable electrode 57 to have contact with the outside.

It is preferable that the stretchable cover 61 is made from an insulating material having stretchability. For example, an elastomer material may be used for the stretchable cover 61, and it may be possible to use the same resin material as the stretchable base 53. With this configuration, it is possible to protect the stretchable wiring 55 without deteriorating stretchability of the stretchable area 50 on the stretchable circuit board 300. The stretchable cover 61 can be manufactured by coating the film base 33 and the stretchable base 53 with an elastomer-based paste and drying them. Alternatively, it may be possible to affix the stretchable cover 61 formed into a sheet shape in advance to the film base 33 and the stretchable base 53, or it may be possible to join them using an adhesive.

There is no particular limitation to the thickness of the stretchable cover 61. However, the thickness of the stretchable cover 61 is set preferably to not more than 100 μm, more preferably to not more than 50 μm, and still more preferably to not more than 30 μm from the viewpoint of avoiding restriction to stretchability of the stretchable circuit board 300.

With the stretchable cover 61 being provided, it is possible to cause the entire stretchable base 53 to stretch in a relatively uniform manner when the stretchable circuit board 300 is stretched in in-plane directions, and also to prevent the stretchable wiring 55 from breaking. Furthermore, in the third exemplary embodiment, the stretchable supporting member 41 is formed so as to additionally cover the area where the stretchable cover 61 extends over the stretchable portion 50 and non-stretchable portion 30, and hence, the stress concentration occurring on the end edge of the stretchable cover 61 is distributed by the non-stretchable portion 30. This makes it possible to further prevent the stretchable wiring 55 from breaking. In addition, the stretchable wiring 55 is sandwiched by the stretchable cover 61 and the stretchable base 53 in the thickness direction, and hence, the stretchable wiring 55 in the stretchable portion 50 is positioned substantially at the center of the stretchable circuit board 300. Thus, when the stretchable circuit board 300 is bent in the surface-normal direction, the tensile stress and the compressive stress, each of which acts on the stretchable wiring 55, are canceled, so that the stretchable wiring 55 can be protected.

Furthermore, the third exemplary embodiment is not limited to the configuration in which the stretchable supporting member and the stretchable cover are provided on the upper portion of the non-stretchable portion 30 and the stretchable portion 50. The stretchable supporting member and the stretchable cover may be provided at the lower portion opposite to the upper portion of the non-stretchable portion 30 and the stretchable portion 50 illustrated in FIGS. 1A and 1B. A stretchable cover 63 illustrated in FIGS. 6A and 6B, together with the stretchable supporting member 43, covers the non-stretchable portion 30 and the stretchable portion 50 from the lower surfaces of the non-stretchable portion 30 and the stretchable portion 50 in the drawings. In addition, the stretchable cover 63 has a main surface 63a that is in contact with the stretchable supporting member 43, and a main surface 63b that is in contact with the stretchable base 53. The stretchable cover 63 has an opening 63d for the stretchable electrode 57 to have contact with the outside, and an opening 63c for the connection end portion 38 (FIG. 1A, FIG. 1B, and FIG. 2) to have contact with the outside. The stretchable supporting member 43 has an opening 43a for the connection end portion 38 (FIG. 1A, FIG. 1B, and FIG. 2) to have contact with the outside.

Figure 6A:
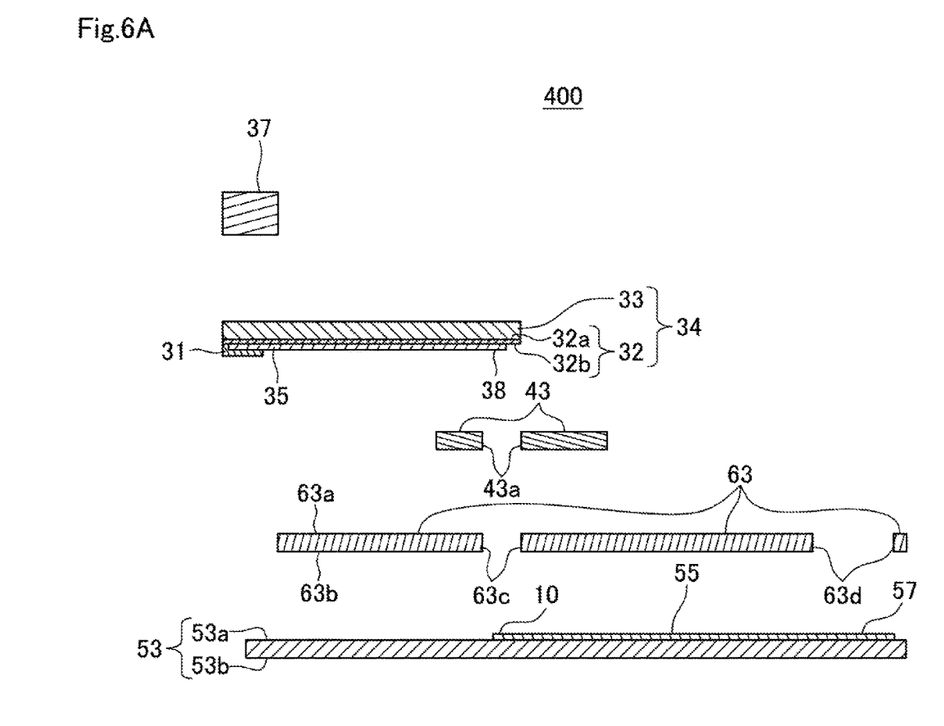
FIGS. 6A and 6B are diagrams for explaining another configuration example of the stretchable circuit board according to the third exemplary embodiment illustrated in FIGS. 5A and 5B.
Figure 6B:
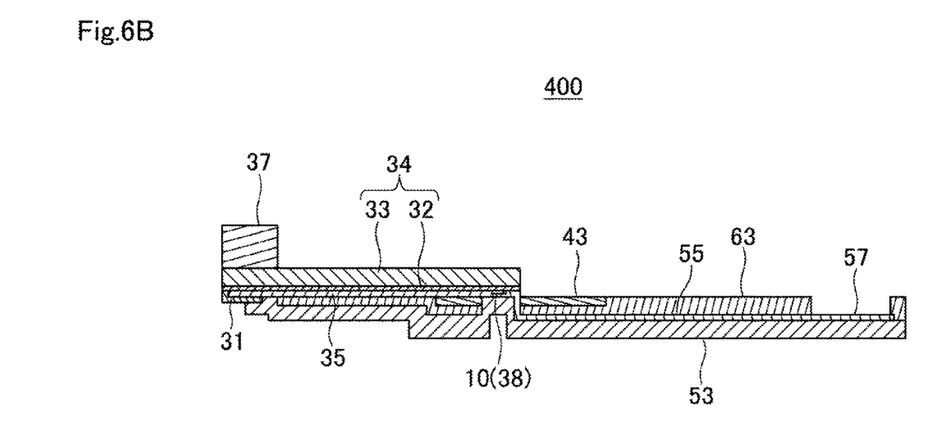

In the stretchable circuit board 400 illustrated in FIGS. 6A and 6B, part of the main surface 32b of the anchor layer 32 is joined with the stretchable supporting member 43 and the stretchable cover 63. Since the surface of the main surface 32b is the rough surface r, it is possible to obtain an increased joining strength of the anchor layer 32 with the stretchable supporting member 43 and the stretchable cover 63 in the stretchable circuit board 400.

With the stretchable circuit board 400 illustrated in FIGS. 6A and 6B, it is possible to prevent the stretchable wiring 55 from breaking when the stretchable circuit board 400 is stretched in in-plane directions, as with the stretchable circuit board 300 illustrated in FIGS. 5A and 5B. In addition, when the stretchable circuit board 400 is bent in the surface-normal direction, the tensile stress and the compressive stress, each of which acts on the stretchable wiring 55, are canceled, so that the stretchable wiring 55 can be protected.

The exemplary embodiments described above include the following technical ideas.

(1) A stretchable circuit board, including:
a stretchable portion that includes a stretchable base having stretchability and a stretchable wiring formed on a first main surface of the stretchable base and having stretchability; and
a non-stretchable portion that includes a base substrate having stretchability lower than that of the stretchable base and a draw-out wiring formed on a first main surface of the base substrate, in which
the first main surface of the stretchable base and the first main surface of the base substrate are joined with each other,
the stretchable wiring and the draw-out wiring are electrically connected with each other, and
the first main surface of the base substrate is a rough surface having projections and depressions.

(2) The stretchable circuit board according to (1), in which
the base substrate includes a film-like film member and an anchor layer provided between the film member and the draw-out wiring, and
a first main surface of the anchor layer is the rough surface.

(3) The stretchable circuit board according to (1) or (2), in which
a stretchable supporting member having stretchability equivalent to that of the stretchable base and higher than that of the base substrate is provided in an area including a boundary between the stretchable portion and the non-stretchable portion.

(4) The stretchable circuit board according to any one of (1) to (3), in which
a surface roughness of the rough surface of the base substrate has an average roughness that falls in a range of not less than 0.5 μm and not more than 5 μm.

(5) The stretchable circuit board according to any one of (1) to (4), in which,
in addition to the first main surface of the base substrate, a back surface of the base substrate corresponding to the main surface is a rough surface having projections and depressions.

(6) The stretchable circuit board according to (5), in which
the average roughness of the first main surface of the base substrate is substantially equal to the average roughness of the back surface of the base substrate.

(7) The stretchable circuit board according to (5) or (6), in which
a stretchable cover that covers at least part of the stretchable wiring and having stretchability is joined directly with the back surface of the base substrate.

(8) The stretchable circuit board according to any one of (1) to (7), in which
the draw-out wiring is made of a material containing copper, and
a connecting portion between the draw-out wiring and the stretchable wiring is a base made of the material containing copper, or plating with at least one of tin and solder is applied to the connecting portion.

(9) The stretchable circuit board according to any one of (1) to (8), in which
a terminal to be electrically connected with the draw-out wiring is provided on the first main surface of the non-stretchable portion, and
gold plating is applied to the terminal.

(10) The stretchable circuit board according to (9), in which
a reinforcing member is provided on a back side of a position where the terminal is formed.

(11) A method for manufacturing a stretchable circuit board, which includes:
etching a metal foil of a base substrate and exposing a rough surface having a projection and a depression, the base substrate including the rough surface and the metal foil formed on the rough surface; and bonding a stretchable portion, which includes a stretchable base having stretchability higher than that of the base substrate and also includes a stretchable wiring formed on a first main surface of the stretchable base and having stretchability, to the base substrate such that the stretchable base and the stretchable wiring are joined with the rough surface.

EXPLANATION OF REFERENCE CHARACTERS 10 joining portion
30 non-stretchable portion
31 external terminal
32 anchor layer
32a, 32b, 33a, 33b, 53a, 63a, 63b main surface
33 film base
34 base substrate
35 draw-out wiring
37 reinforcing member
38 connection end portion
41, 43 stretchable supporting member
43a, 61a, 63c, 63d opening
50 stretchable portion
53 stretchable base
55 stretchable wiring
57 stretchable electrode
61, 63 stretchable cover
100, 200, 300, 400 stretchable circuit board

The invention claimed is:

1. A stretchable circuit board, comprising:
a stretchable portion that includes a stretchable base having stretchability and a stretchable wiring formed on a first main surface of the stretchable base and having stretchability; and
a non-stretchable portion that includes a base substrate having stretchability lower than that of the stretchable base and a draw-out wiring formed on a first main surface of the base substrate, wherein
the first main surface of the stretchable base and the first main surface of the base substrate are joined with each other,
the stretchable wiring and the draw-out wiring are electrically connected with each other, and
the first main surface of the base substrate is a rough surface having a projection and a depression.

2. The stretchable circuit board according to claim 1, wherein
the base substrate includes a film-like film member and an anchor layer provided between the film member and the draw-out wiring, and
a first main surface of the anchor layer is the rough surface.

3. The stretchable circuit board according to claim 1, wherein
a stretchable supporting member having stretchability equivalent to that of the stretchable base and higher than that of the base substrate is provided in an area including a boundary between the stretchable portion and the non-stretchable portion.

4. The stretchable circuit board according to claim 1, wherein
a surface roughness of the rough surface of the base substrate has an average roughness that falls in a range of not less than 0.5 μm and not more than 5 μm.

5. The stretchable circuit board according to claim 1, wherein,
in addition to the first main surface of the base substrate, a back surface of the base substrate corresponding to the main surface is a rough surface having a projection and a depression.

6. The stretchable circuit board according to claim 5, wherein
the average roughness of the first main surface of the base substrate is substantially equal to the average roughness of the back surface of the base substrate.

7. The stretchable circuit board according to claim 5, wherein
a stretchable cover that covers at least part of the stretchable wiring and having stretchability is joined directly with the back surface of the base substrate.

8. The stretchable circuit board according to claim 1, wherein
the draw-out wiring is made of a material containing copper, and
a connecting portion between the draw-out wiring and the stretchable wiring is a base made of the material containing copper, or plating with at least one of tin and solder is applied to the connecting portion.

9. The stretchable circuit board according to claim 1, wherein
a terminal to be electrically connected with the draw-out wiring is provided on the first main surface of the non-stretchable portion, and
gold plating is applied to the terminal.

10. The stretchable circuit board according to claim 9, wherein
a reinforcing member is provided on a back side of a position where the terminal is formed.

11. A method for manufacturing a stretchable circuit board, comprising:
etching a metal foil of a base substrate and exposing a rough surface having a projection and a depression, the base substrate including the rough surface and the metal foil formed on the rough surface; and
bonding a stretchable portion, which includes a stretchable base having stretchability higher than that of the base substrate and also includes a stretchable wiring formed on a first main surface of the stretchable base and having stretchability, to the base substrate such that the stretchable base and the stretchable wiring are joined with the rough surface.

* * * * *